US006409701B1

(12) United States Patent
Cohn et al.

(10) Patent No.: US 6,409,701 B1
(45) Date of Patent: Jun. 25, 2002

(54) HYPODERMIC SYRINGE WITH SELECTIVELY RETRACTABLE NEEDLE

(75) Inventors: Simon Cohn, N. Arlington, NJ (US);
Roger Hoeck, Holdrege, NE (US);
Richard Caizza, Pompton Lakes;
Volker Niermann, Little Falls, both of NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 74 days.

(21) Appl. No.: 09/677,050

(22) Filed: Sep. 29, 2000

(51) Int. Cl.$^7$ ................................................ A61M 5/00
(52) U.S. Cl. ........................................ 604/110; 604/195
(58) Field of Search ................................ 604/110, 195, 604/198, 192, 187, 218, 263, 228; 128/919

(56) References Cited

U.S. PATENT DOCUMENTS

| | | |
|---|---|---|
| 4,233,975 A | 11/1980 | Yerman |
| 4,838,863 A | 6/1989 | Allard et al. |
| 4,838,869 A | 6/1989 | Allard |
| 4,900,307 A | 2/1990 | Kulli |
| 4,927,414 A | 5/1990 | Kulli |
| 4,929,237 A | 5/1990 | Medway |
| 4,946,446 A | 8/1990 | Vadher |
| 4,955,870 A | 9/1990 | Ridderheim et al. |
| 4,966,593 A | 10/1990 | Lennox |
| 4,973,316 A | 11/1990 | Dysarz |
| 4,994,034 A | 2/1991 | Botich et al. |
| 5,011,476 A | 4/1991 | Foster |
| 5,013,301 A | 5/1991 | Marotta, Jr. et al. |
| 5,019,044 A | 5/1991 | Tsao |
| 5,045,063 A | 9/1991 | Spielberg |
| 5,046,508 A | 9/1991 | Weissler |
| 5,047,017 A | 9/1991 | Koska |
| 5,049,133 A | 9/1991 | Villen Pascual |
| 5,053,010 A | 10/1991 | McGary et al. |
| 5,064,419 A | 11/1991 | Gaarde |
| 5,084,018 A | 1/1992 | Tsao |
| 5,084,029 A | 1/1992 | Nacci nee Tagliaferri et al. |
| 5,085,640 A | 2/1992 | Gibbs |
| 5,092,853 A | 3/1992 | Couvertier, II |
| 5,114,410 A | 5/1992 | Caralt Batle |
| 5,180,369 A | 1/1993 | Dysarz |
| 5,180,370 A | 1/1993 | Gillespie |
| 5,188,599 A | 2/1993 | Botich et al. |
| 5,201,710 A | 4/1993 | Caselli |
| 5,211,629 A | 5/1993 | Pressly et al. |
| 5,232,447 A | 8/1993 | Schwarz et al. |
| 5,232,456 A | 8/1993 | Gonzalez |
| 5,267,961 A | 12/1993 | Shaw |
| 5,267,976 A | 12/1993 | Guerineau et al. |

(List continued on next page.)

Primary Examiner—Anhtuan T. Nguyen
(74) Attorney, Agent, or Firm—Arthur D. Dawson

(57) ABSTRACT

A retractable needle syringe includes a barrel defining a receiver. There is a plunger having an inner rod extending distally from the proximal end. The plunger includes a hollow sleeve that is disposed over and extend beyond an inner rod. The plunger includes a hollow cutter extending from the inner rod and a stopper disposed over the end of the sleeve. The plunger has a displaceable collar to prevent movement of the inner rod with respect to the sleeve, that is by distal force to the plunger by engagement with the proximal end of the barrel allowing the cutting surface to cut through the stopper. There is a hub with a stem, a proximal flange and an engagement. A clip having a proximal foot with an opening therethrough and a distal grip is disposed on the stem of the hub. The proximal foot of the clip is disposed at the distal surface of the flange and the grip at the engagement on the stem. There is a spring disposed about the stem compressed between the receiver and the clip to provide a bias, so that when sufficient force is applied to the plunger causing the cutting surface to cut through the stopper, the cutting surface then engages, cuts through the flange to engage the clip and cause the clip to release the engagement on the stem. This allows the spring to urge the hub to a position within the syringe.

19 Claims, 17 Drawing Sheets

U.S. PATENT DOCUMENTS

| | | |
|---|---|---|
| 5,342,308 A | 8/1994 | Boschetti |
| 5,376,080 A | 12/1994 | Petrussa |
| 5,385,551 A | 1/1995 | Shaw |
| 5,389,076 A | 2/1995 | Shaw |
| 5,395,337 A | 3/1995 | Clemens et al. |
| 5,407,431 A | 4/1995 | Botich et al. |
| 5,407,436 A | 4/1995 | Toft et al. |
| 5,423,758 A | 6/1995 | Shaw |
| 5,487,732 A | 1/1996 | Jeffrey |
| 5,531,694 A | 7/1996 | Clemens et al. |
| 5,542,927 A | 8/1996 | Thorne et al. ............ 604/110 |
| 5,562,629 A | 10/1996 | Haughton et al. ......... 604/158 |
| 5,573,510 A | 11/1996 | Isaacson .................... 604/158 |
| 5,575,777 A | 11/1996 | Cover et al. ............... 604/198 |
| 5,578,011 A | 11/1996 | Shaw ......................... 604/110 |
| 5,605,544 A | 2/1997 | Tsao .......................... 604/110 |
| 5,613,952 A | 3/1997 | Pressly, Sr. et al. ....... 604/110 |
| 5,632,733 A | 5/1997 | Shaw ......................... 604/195 |
| 5,634,909 A | 6/1997 | Schmitz ..................... 604/196 |
| 5,637,092 A | 6/1997 | Shaw ......................... 604/110 |
| 5,643,211 A | 7/1997 | Sadowski et al. .......... 604/110 |
| 5,681,292 A | 10/1997 | Tober et al. ................ 604/195 |
| 5,685,863 A | 11/1997 | Botich et al. .............. 604/198 |
| 5,769,822 A | 6/1998 | McGary et al. ............. 604/110 |
| 5,782,804 A | 7/1998 | McMahon ................. 604/110 |
| 5,788,677 A | 8/1998 | Botich et al. .............. 604/195 |
| 5,792,107 A | 8/1998 | Petrocelli ................... 604/110 |
| 5,800,395 A | 9/1998 | Botich et al. .............. 604/110 |
| 5,800,403 A | 9/1998 | Pressly, Sr. et al. ........ 604/195 |
| 5,853,390 A | 12/1998 | Freschi ...................... 604/110 |
| 5,882,342 A | 3/1999 | Cooper et al. ............. 604/195 |
| 5,885,257 A | 3/1999 | Badger ...................... 604/195 |
| 5,935,104 A | 8/1999 | Janek et al. ................ 604/110 |
| 5,984,898 A | 11/1999 | Garvin ....................... 604/195 |
| 6,004,278 A | 12/1999 | Botich et al. .............. 600/576 |

HYPODERMIC SYRINGE WITH SELECTIVELY RETRACTABLE NEEDLE

FIELD OF INVENTION

The present invention is generally related to hypodermic syringes and more particularly to syringes that include a needle that is retractable after the intended use to substantially prevent inadvertent exposure to the needle and reuse of the syringe.

BACKGROUND

Hypodermic syringes are widely used in the medical arts for administering medicaments and for drawing body fluid samples. Generally, hypodermic syringes have a metal needle attached either fixedly or removably that has a sharpened distal point for penetrating vial stoppers or patient's skin. The hypodermic syringes and needles have been used for many years with few problems reported when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needles and syringes, syringes and needles that include provisions to prevent reuse have been developed.

Provisions intended to prevent reuse of needles and syringes include a variety of sharps collector systems that are widely used in health care facilities. Other developments include needle attachments that may be readily broken off by practitioners once the syringe has completed its intended use. A variety of shielding mechanisms has been developed; some of which are currently commercially available. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed.

U.S. Pat. No. 4,838,869 discloses a retractable hypodermic needle configured for one-time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. A potential problem with the design disclosed in this patent is that many times a practitioner may draw and expel a fluid several times during preparation for administration of a medicament, with this design, the practitioner could inadvertently discharge the retraction mechanism. Further, the design would be very difficult to manufacture in large volumes.

U.S. Pat. No. 4,900,307 discloses a hypodermic needle with an enlarged hub that provides provisions for selectively withdrawing the needle into the hub once the syringe and needle have completed their intended usage. While this disclosed design does substantially eliminate the problem of premature discharge of the retraction mechanism, the enlarged hub has a considerable "dead volume" that would result in a significant undeliverable retention of the medicament. Additionally, although the needle is secured in the hub after discharge, the syringe itself is still fully functional after the hub with the needle inside is removed.

U.S. Pat. No. 4,994,034 discloses a hypodermic injection system with a retractable needle wherein the needle retracts within the interior cavity of a syringe plunger. The disclosed invention includes a cylindrical spring housing with resilient fingers which capture a coiled spring that biasly holds a needle holder against the retaining force of the resilient fingers. The plunger in this disclosure has a frangible end, which when engaging the resilient fingers under a predetermined amount of force, dissociate the remaining inwardly-tapered shoulders to spread the resilient fingers, allowing the coiled spring to eject the needle and its holder into the interior cavity of the syringe plunger. A syringe manufactured using this disclosure would be complex and difficult to assemble. It is believed that no successful commercial product has been produced using this disclosure.

U.S. Pat. No. 5,019,044 discloses a safety hypodermic syringe with a hypodermic needle fixed connected to a holder plate and constantly supported by a spring for making axial movement. The holder plate is normally retained by a clamp at a ready position for injection. When the plunger of the syringe is pushed to the bottom of the barrel, the needle is released from the clamp and is pushed by the spring to drop and further follow a rubber plug to be squeezed into a chamber in the plunger. Again, no successful commercial product has resulted from this disclosure, which would be complex to manufacture and appears to have a considerable undeliverable dead volume.

Another example of a syringe with a retractable needle is disclosed in U.S. Pat. No. 5,053,010. The disclosed syringe retracts the needle into a hollow plunger when additional pressure is applied on the plunger after the contents of the syringe are expelled. The disclosed design incorporates a sliding elastomeric seal which displaces from its forward position to a retracted position, thereby allowing additional forward travel of the plunger to actuate the retraction mechanism. A problem reported with this design is that, because of the soft nature of the seal, the seal may be prematurely displaced during its use in an injection. Attempts to overcome this difficulty by increasing the stiffness of the sealing member could impair the seal integrity.

U.S. Pat. No. 5,180,369 discloses a self destructive syringe assembly having a needle cannula fixed to a slidable piston. The slidable piston and slidable piston flange are held within the barrel of the syringe assembly by a compressed spring, a guide tube and a shatter ring. The plunger of the syringe assembly is a hollow elongated tube with a thumb flat at one end, a sliding gasket, a plunger shatter plate and a hook rim at the other end. The patent reports that when medicament is injected, the elongated hollow plunger is further thrust into the shatter ring, the shatter ring shatters, further allowing the slidable piston and slidable piston flange to thrust into the plunger shatter plate to shatter. The shattering of the plunger shatter plate causes the slidable piston and needle cannula to be thrust into the hollow plunger by the spring and is thus prevented from re-entering the guide tube. Again, no successful commercial product has resulted from this disclosure.

U.S. Pat. No. 5,180,370 discloses a syringe which has an internal mechanism for retracting the needle into the syringe after the injection has been given. In one disclosed embodiment, the needle is manually retracted by pulling back on the plunger, and in another, the needle is propelled by a compressed spring into a hollow chamber within the plunger. A syringe produced with this disclosure would be complex to manufacture, and no successful commercial product has resulted from this disclosure.

U.S. Pat. No. 5,188,599 discloses a hypodermic injection system with a needle that retracts within an interior cavity of the syringe plunger. The needle when retracted is held within the plunger. The disclosed device includes a cylindrical spring housing that has resilient fingers which capture a spring under bias holding a needle holder against the retaining force of resilient fingers. The plunger has a frangible end which dissociates when the outwardly tapered shoulders spread the resilient fingers, allowing the coiled spring to eject the needle and its holder into the interior cavity of the syringe plunger. The patent also discloses a body fluid sampling device that includes a double-ended needle for communication with an evacuated blood collection tube. This patent also includes a review of several earlier disclosures related to retractable needles. Attempts have been made to produce commercial products based on the disclosures of this patent, but as yet there is no successful commercial product.

U.S. Pat. No. 5,201,710 discloses a syringe fitted with a clamping device for the needle and with a mechanism to enable the needle to be automatically retractable into the syringe body at the end of an injection. The disclosed device includes inner and outer cylinders, openings at the ends of the outer cylinder, a third opening at an end of the inner cylinder and a closure for the third opening. The disclosed device further includes a needle with a head, a seal, a first spring to push the needle against the closure and a clamping device loaded by a second spring to maintain outward to the syringe and to release the needle. There is a diaphragm in the closure that bends before breaking and a sharp element to break the diaphragm. There also is a closure to prevent the needle from being accessible and a stop to prevent the second cylinder from being moved outwardly after the syringe is used. As is apparent from the description, the device disclosed by this patent is complex and would be difficult to assemble. No successful commercial product has resulted from the disclosure in this patent.

U.S. Pat. No. 5,385,551 discloses a non-reusable medical device that has a needle which is retractable by depression a plunger slidably mounted in the device. The disclosed device includes a front-mounted retraction mechanism that has a needle holder connected to the needle. The needle holder is supported along the axis of the device by a frictionally engaged retainer ring member coupled to the needle holder along an axially aligned sliding interface. The needle holder and retainer are positioned in the front portion of a hollow body. The front of a movable member or plunger presses against the retainer member passing around the needle holder which cannot move forward, thereby separating the retainer from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring. Again, the device disclosed in this patent is complex, difficult to manufacture and appears to have significant undeliverable dead volume. Attempts have been made to commercialize products from this disclosure with only limited success.

U.S. Pat. No. 5,407,436 discloses a hypodermic syringe that has a hollow needle that is automatically retractable after use. The disclosed syringe includes a one-piece body molding that has a main chamber for a plunger, sample container or drug cartridge, a forward chamber to house a spring to bias a needle holder, and internal latching formations to retain the needle holder with the spring compressed in the forward chamber until automatic retraction when the latching formations are released by end of plunger movement. The patent discloses that the sealing between the plunger and the body is accomplished by an over-sized plunger head that forces head and wall deformation. The disclosed spring has seals at both ends for the forward chamber. The patent teaches that the needle, its holder, spring and seals can be installed using a sliding guide. In using a syringe produced using this disclosure, the practitioner would need to exercise care when drawing and expelling a fluid during filling, because the retraction of the needle is activated by depressing the plunger sufficiently to engage cooperating latches. The engagement occurs at the bottom of the stroke to expel fluid from the syringe.

U.S. Pat. No. 5,769,822 discloses a non-reusable syringe with a hollow plunger that has a seal member thereon. The position of the plunger and the seal relative to the barrel permits the plunger, with sufficient strength, to carry applied pressure through the device during injection of a fluid and yet permit the seal disposed at one end of the plunger to have maximum sealing integrity between the plunger and a cylindrical barrel disposed around the exterior of the plunger to abate leakage of the liquid in a chamber within the barrel, as the plunger is manipulated from an expanded position to and expended position and thereafter to a third or collapsed position.

U.S. Pat. No. 6,010,486 discloses a retracting needle syringe that substantially prevents reuse of the syringe by destroying the plunger rod and the needle hub and additionally, retracts the needle into the plunger rod. The disclosed syringe includes provisions that upon fully depressing the plunger rod and applying distally directed axial force, a frangible portion of the inner hub is broken and the plunger tip dislodges to allow a spring to urge a cutter to open the chamber inside the plunger.

Most of the devices discussed in the above referenced disclosures are somewhat complex, and many require manufacture and assembly of parts with potentially difficult assembly or tight tolerance requirements. Many of the designs depend upon a careful application of forces by the practitioner to draw and expel fluids from the syringe. Also, if the tolerances between the multiple components of the device are not carefully adhered to during manufacture and assembly, normal usage may result in premature activation of the retraction function of the syringe. Current conventional syringes are considered by users to be virtually fault-free and reliable. They are used for a variety of different procedures involving both "one-shot" fill and inject procedures, as well as more complex mixing measuring and delivery functions. In order for a retractable syringe to displace these functional, utilitarian and reliable conventional syringes, the retractable syringe should not significantly interfere with the users current practices, it needs to be substantially reliable and their cost should not be prohibitive. Current conventional syringes are often manufactured at rates of several hundred per minute and their cost is generally not a significant factor in their usage. Additionally every year, hundreds of millions of small capacity (one milliliter) syringes are used outside of the normal controlled health care environment by diabetics and other self-injectors who must daily accurately inject small amounts, often only a few tenths of a milliliter. These small capacity syringes are physically quite small, with an overall length of less than five inches and an inside bore diameter of less than one-quarter inch. Reviewing the disclosures above, one skilled in the art of high volume manufacturing recognizes that assembling hundreds of millions of most of these relatively complex devices with their retraction elements contained in such a small space as a one-quarter inch diameter bore is a daunting task. Additionally, many of the disclosed devices have substantial undeliverable "dead volumes" that substantially confound many diabetics' need for accurate measuring, mixing of more than one type of insulin in the syringe and delivering small doses of insulin. The need thus exists for a selectively retractable syringe that is compatible with a small capacity syringe, that is capable of being manufactured at high volumes and is sufficiently non-complex to be reliable in use when produced at volumes of hundreds of millions per year. Such a device is disclosed herein below.

SUMMARY

A hypodermic syringe with a selectively retractable needle of the present invention includes an elongate barrel with an open proximal end and a distal end defining a receiver having a distal inward shoulder. The barrel has a hollow bore therethrough extending from the proximal end to the distal end. The syringe has an elongate plunger having a proximal end, a distal end and an inner rod extending a distance distally from the proximal end. The plunger includes a hollow sleeve having a proximal end and a distal end, that is sized to fit slidably, extend beyond and disposed over the inner rod. The plunger also includes a hollow cutter extending distally from the inner rod to a distal cutting surface within the hollow sleeve, and a stopper disposed over the distal end of the hollow sleeve to cover the cutting surface. The stopper is sized to fit slidably within the hollow bore of the barrel to define a chamber to draw and expel fluid. The plunger further includes a displaceable collar that substantially prevents a movement of the inner rod with respect to the hollow sleeve, the collar being displaced by application of a distal force, greater than a force required to expel fluid from the chamber in the barrel, to the plunger. The collar is displaced by engagement with the proximal end of the barrel, and, when the collar is displaced, movement of the inner rod having the cutter attached thereto with respect to the hollow sleeve is allowed, and causes the cutting surface to cut through the stopper. The syringe further includes an elongate hub with a passageway therethrough and a stem with a proximal flange and an engagement. The stem is disposed within and sized for slidable movement within the receiver at the distal end of the barrel. The flange on the hub has a distal surface and a proximal surface defining a distal end of the chamber in the barrel. There is a clip having a proximal foot with an opening therethrough and a distal grip disposed on the stem of the hub. The proximal foot of the clip is disposed at the distal surface of the flange and the grip at the engagement on the stem. The syringe includes an elongate needle having a fluid path therethrough, a pointed distal end and a proximal end mounted in the passageway of the hub so that the pointed end of the needle extends distally outwardly and the fluid path of the needle is in fluid communication with the chamber of the barrel. There is an elongate spring disposed about the stem of the hub compressed between the receiver and the distal grip of the clip to provide a bias, so that when sufficient distal force, greater than the force needed to expel fluid from the chamber, is applied to the plunger to cause the cutting surface to cut through the stopper, the cutting surface then engages the flange and cuts through the flange to engage the clip and to cause the clip to release the engagement on the stem. The release allows the bias of the spring to urge a sufficient movement of the hub to a position within the syringe where inadvertent contact with the pointed distal end of the needle is substantially prevented.

The syringe of the invention has an undeliverable "dead-space" volume substantially similar to conventional syringes, i.e., substantially no undeliverable volume. The syringe of the invention is as suitable for use in drawing, measuring, mixing and delivering small volumes of medicaments as conventional syringes. Unlike many of the devices disclosed above, the syringe of the invention is substantially unlikely to be inadvertently retracted by a user following currently used practices and procedures. The syringe of the invention does not depend on a user having to exercise substantially more care than with a conventional syringe when drawing and mixing fluids in the syringe to avoid inadvertent activation, and importantly, the syringe of the invention is compatible with the efficiency of high volume automated manufacture that utilizes much existing manufacturing equipment. Once needle is retracted in the syringe of the invention, the syringe cannot be restored to functionality, as the hub flange is cut through and the stopper is cut through rendering the syringe substantially unusable and protecting the needle point from inadvertent contact by anyone.

DETAILED DESCRIPTION

Figure 1:
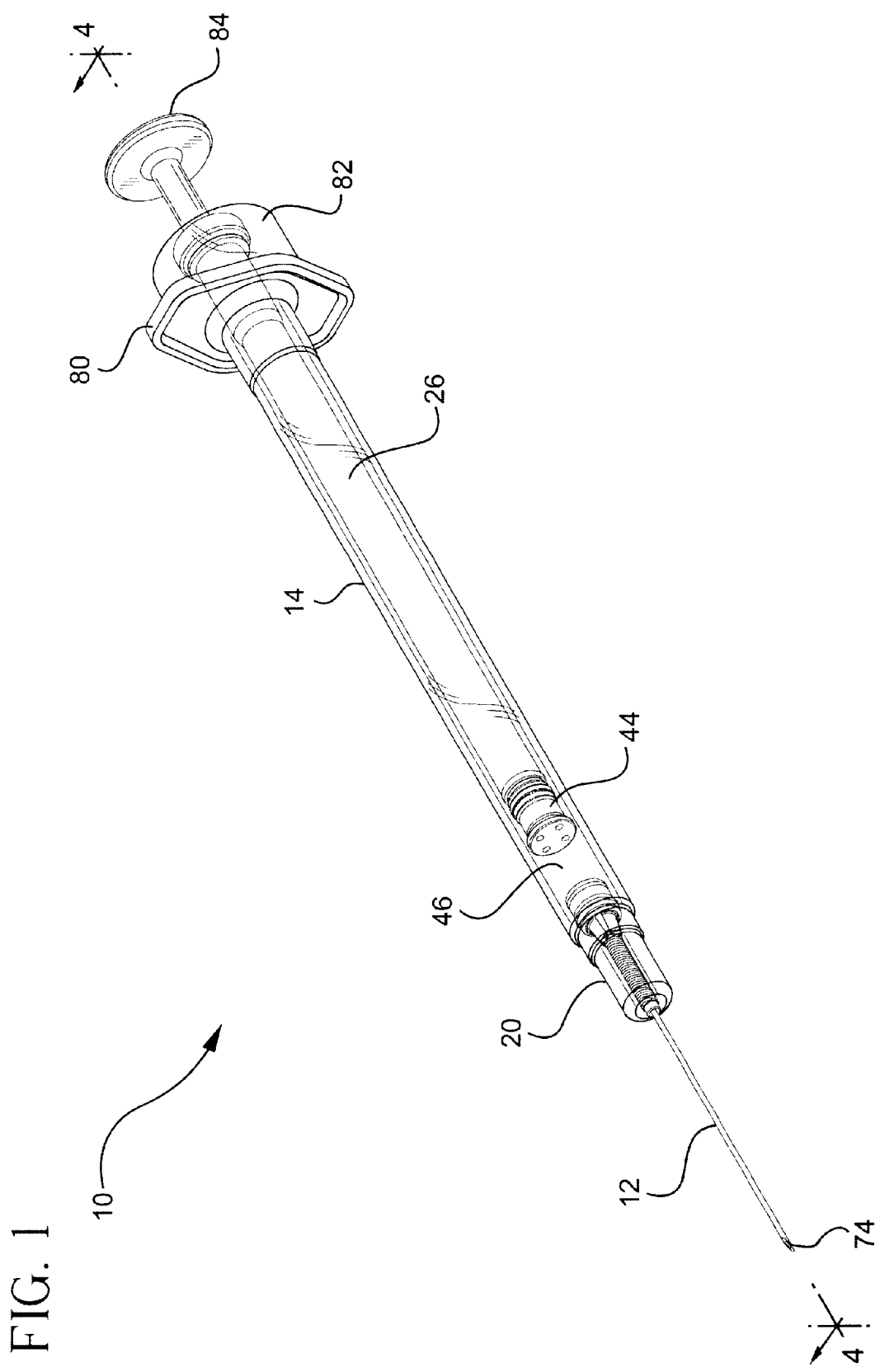
FIG. 1 is a perspective view of the selectively retractable syringe of the invention.
Figure 2:
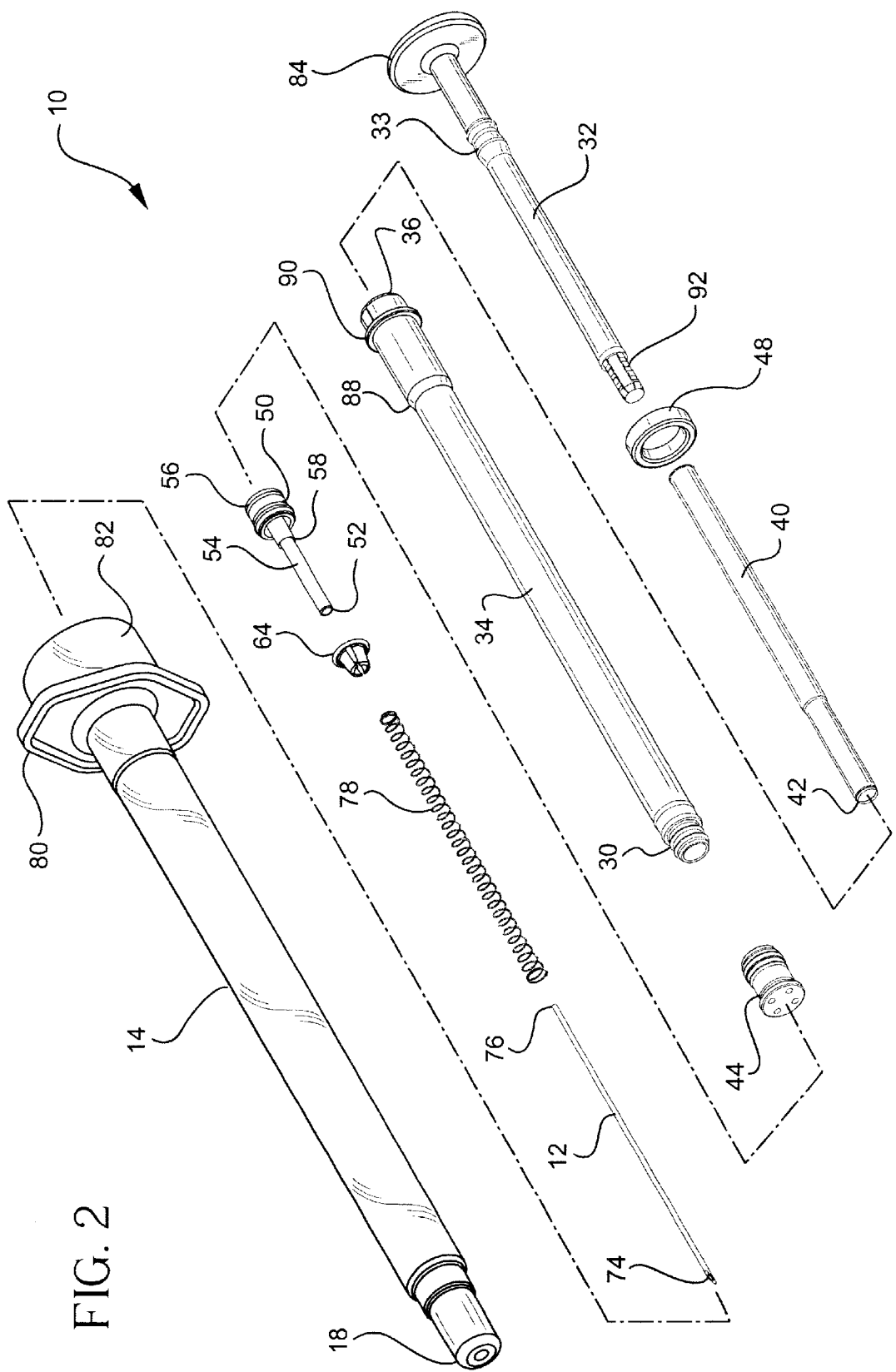
FIG. 2 is an exploded perspective view of the syringe of FIG. 1.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Referring to FIGS. 1–17, a hypodermic syringe 10 with a selectively retractable needle 12 of the present invention includes an elongate barrel 14 with an open proximal end 16 and a distal end 18 defining a receiver 20 having a distal inward shoulder 22. Barrel 14 has a hollow bore 24 therethrough extending from proximal end 16 to distal end 18. Syringe 10 has an elongate plunger 26 having a proximal end 28, a distal end 30 and an inner rod 32 extending a distance distally from proximal end 28. Plunger 26 includes a hollow sleeve 34 having a proximal end 36 and a distal end 38, that is sized to fit slidably, extend beyond and disposed over inner rod 32. Plunger 26 also includes a hollow cutter 40 extending distally from inner rod 32 to a distal cutting surface 42 within hollow sleeve 34, and a stopper 44 disposed over distal end 38 of hollow sleeve 34 to cover cutting surface 42. Stopper 44 is sized to fit slidably within hollow bore 24 of the barrel 14 to define a chamber 46 to draw and expel fluid. Plunger 26 further includes a displaceable collar 48 that substantially prevents a movement of inner rod 32 with respect to hollow sleeve 34, collar 48 being displaced by application of a distal force, greater than a force required to expel fluid from chamber 46 in the barrel, to plunger 26. Collar 48 is displaced by engagement with proximal end 16 of the barrel, and, when collar 48 is displaced, movement of inner rod 32 having cutter 40 attached thereto with respect to the hollow sleeve is allowed, and causes cutting surface 42 to cut through stopper 44. Syringe 10 further includes an elongate hub 50 with a passageway 52 therethrough and a stem 54 with a proximal flange 56 and an engagement 58. Stem 54 is disposed within and sized for slidable movement within receiver 20 at distal end 18 of the barrel. Flange 56 on the hub has a distal surface 60 and a proximal surface 62 defining a distal end of chamber 46 in the barrel. There is a clip 64 having a proximal foot 66 with an opening 68 therethrough and a plurality of distal grips on a plurality of fingers 71 disposed on stem 54 of the hub. Proximal foot 66 of clip 64 is disposed at distal surface 60 of flange 56 and grips 70 at engagement 58 on stem 54. Syringe 10 includes elongate needle 12 having a fluid path 72 therethrough, a pointed distal end 74 and a proximal end 76 mounted in passageway 52 of the hub so that pointed end 74 of the needle extends distally outwardly and fluid path 72 of the needle is in fluid communication with chamber 46 of the barrel. There is an elongate spring 78 disposed about stem 54 of the hub compressed between inward shoulder 22 receiver and distal grips 70 of the clip to provide a bias, so that when sufficient distal force, greater than the force needed to expel fluid from chamber 46, is applied to plunger 26 to cause cutting surface 42 to cut through stopper 44, the cutting surface then engages flange 56 and cuts through the flange to engage clip 64 and to cause the clip to release engagement 58 on stem 54. The release allows the bias of spring 78 to urge a sufficient movement of hub 50 to a position within the syringe where inadvertent contact with pointed distal end 74 of the needle is substantially prevented.

Figure 4:
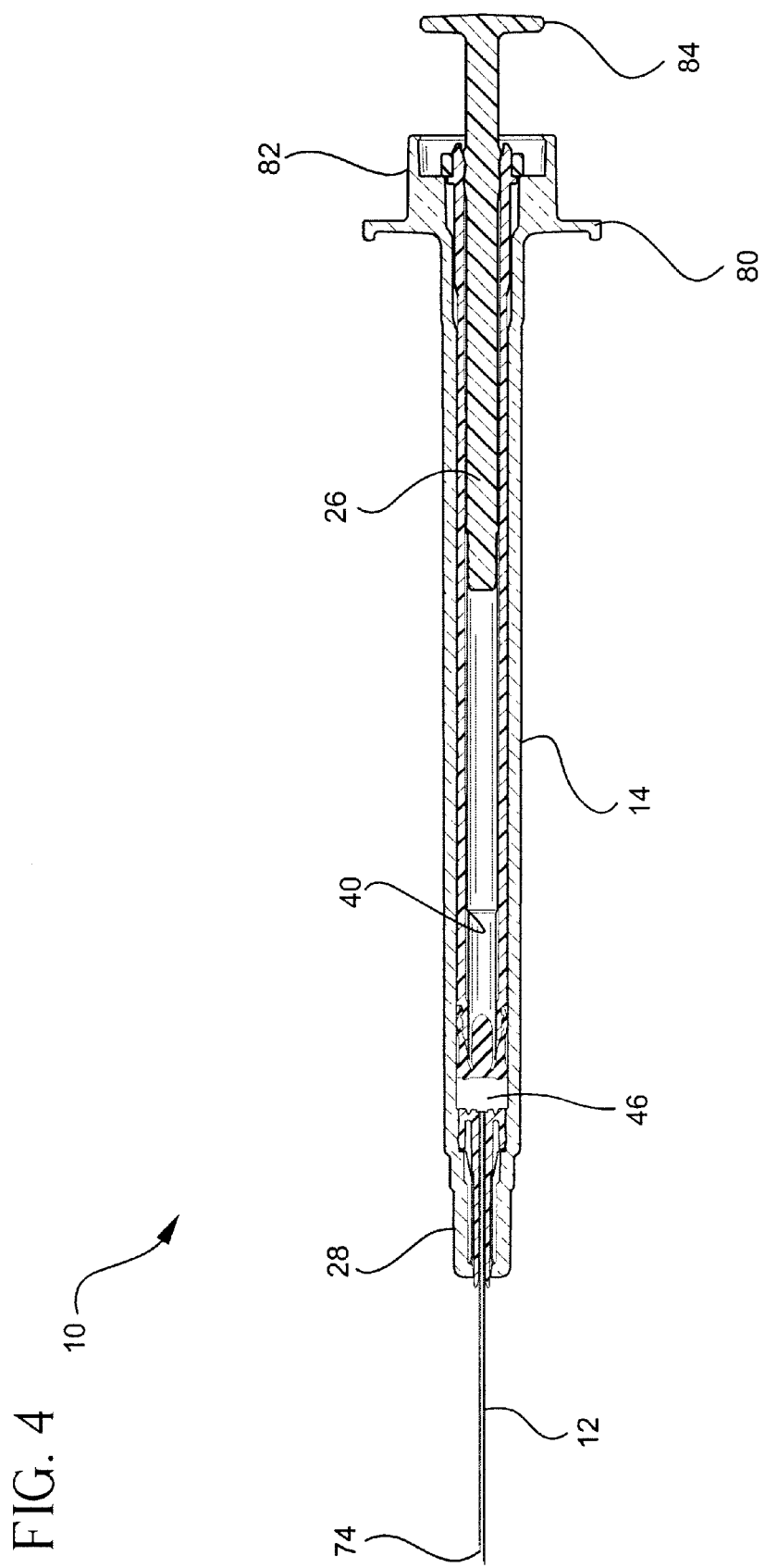
FIG. 4 is a cross-sectional view of the syringe of FIG. 1 taken along the line 4—4.
Figure 5:
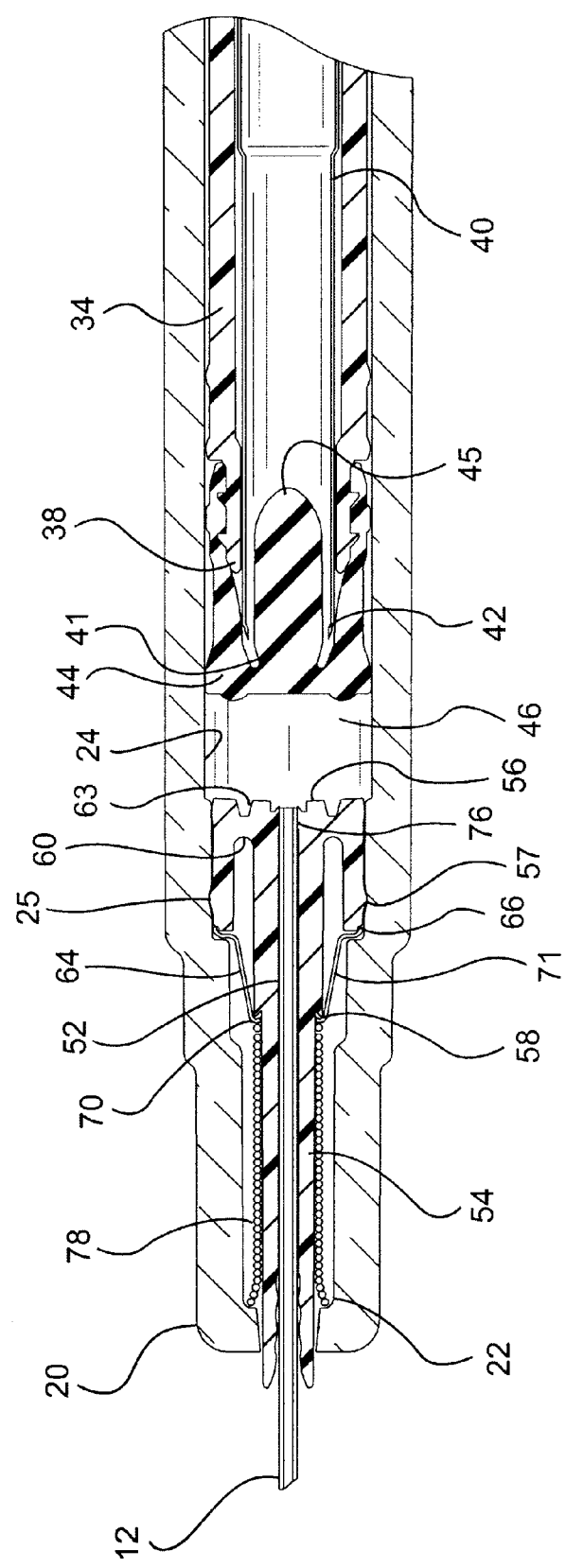
FIG. 5 is an enlarged cross-sectional view of the distal portion of the syringe of FIG. 1 taken from FIG. 4.
Figure 6:
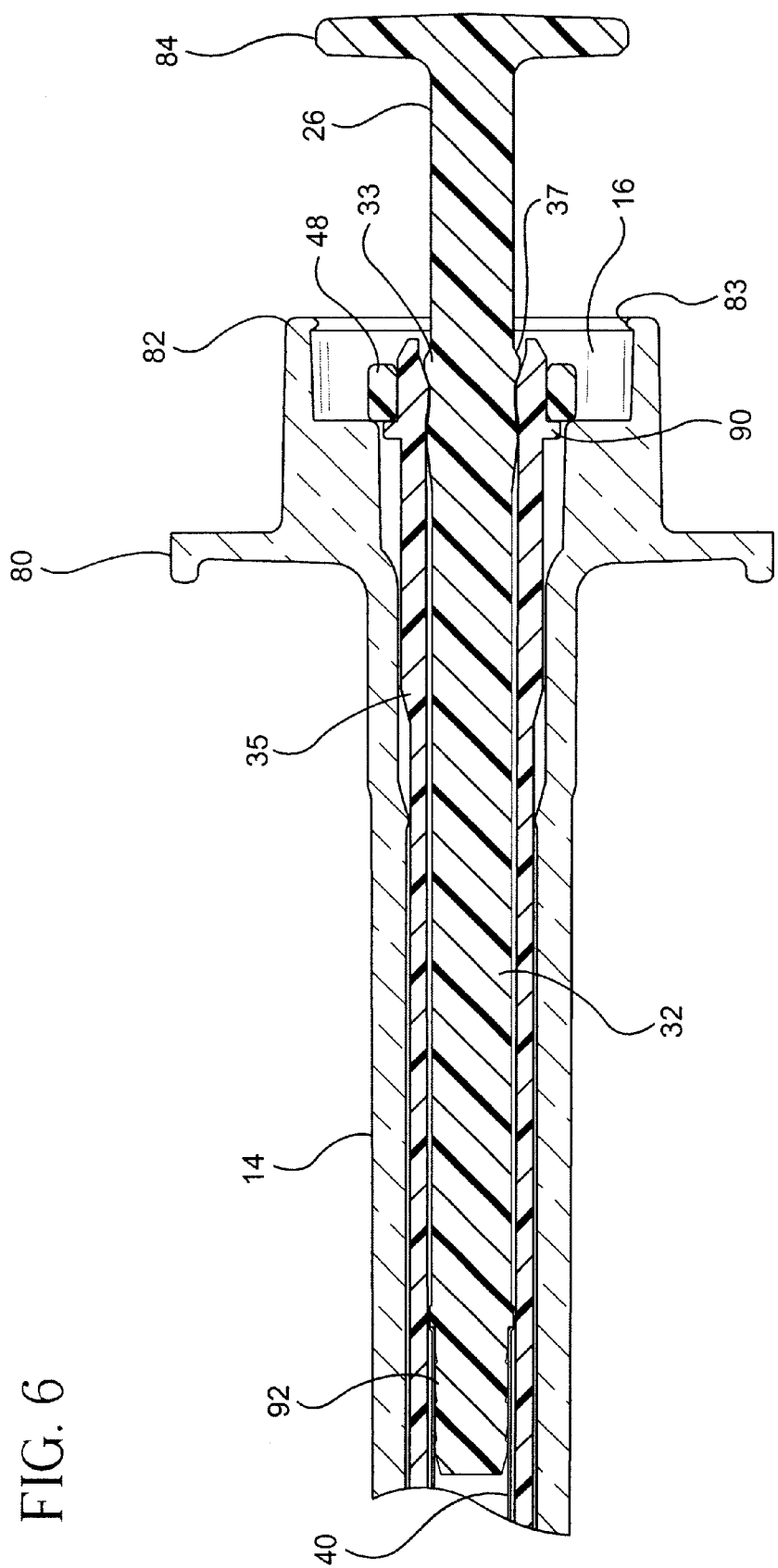
FIG. 6 is an enlarged cross-sectional view of a proximal portion of the syringe of FIG. 1 taken from FIG. 4.

Referring to FIGS. 4–14, a series of cross-sectional views of syringe 10 illustrate the syringe use and selective retraction of needle 12. FIG. 4 is a cross-sectional view of syringe 10 with plunger 26 in an intermediate position in barrel 14 with chamber 46 available to draw and expel fluid with proximal and distal movement of plunger 26. FIG. 5 is an enlargement of the distal portion of FIG. 4. Needle 12, mounted in hub passage 52 is preferably formed from stainless steel and adhesively mounted in passage 52. In this view, stopper 44 is visible at distal end 30 of the plunger with hollow cutter 40 positioned within the plunger proximal to the face of stopper 44. Stopper 44 includes a plug 45 disposed within hollow cutter 40. Plug 45 serves to direct the cut portion of the stopper into the hollow cutter once the retraction sequence of the syringe is initiated. Preferably, stopper 44 includes a cut ring 41. Cut ring 41 has a smaller inside diameter than cutting surface 42 of the hollow cutter. Flange proximal surface 62 preferably includes a cut ring 63 disposed to cooperate with cut ring 41 in the stopper and cutting surface 42 of the hollow cutter. The smaller diameter of cut ring 41 causes cutting surface 42 of the hollow cutter to stretch the face of stopper as it is cut against cut ring 63 of the flange. The stretching of the stopper face results in cutting a smaller slug of the stopper than the diameter of cutting surface 42. The cut slug of stopper 44 is directed into hollow cutter 40 by plug 45. Cooperating cut ring 63 in the flange serves to direct cutting surface 42 to be centered on flange 56 so that cutting surface 42 cuts through flange 56 in the desired location, preferably the region of the thinnest cross section, i.e. at cut ring 63. Flange 56 is preferably retained in the distal position in barrel 14 by an interaction between a distal bump 25 on inside surface of bore 24 of barrel 14 and a depression 57 on hub flange 56. Alternatively, bump 25 can be a depression in barrel bore 24 cooperating with a bump 57 on hub flange 56. The placement of bump 25 on barrel bore 24 is preferred for this application, because a depression in the barrel bore at this point may weaken the barrel. For other applications, other attachments may be preferred and are considered within the scope of the invention. Referring now to FIG. 6, an enlargement of proximal end 28 of the plunger is seen. In this view, a finger flange 80 to facilitate the users grip of the syringe is seen that includes a shroud 82. Plunger 26 preferably includes a finger press 84 at proximal end 28 that, in conjunction with finger flange 80 facilitates the user's movement of the plunger. Inner rod 32 has an enlargement 33, that cooperates with proximal end 36 of hollow sleeve 34 and displaceable collar 48 to substantially prevent movement of inner rod 32 with respect to hollow sleeve 34. As shown in FIG. 6, collar 48 is disposed to retain enlargement 33 within a depression 37 in hollow sleeve 34.

Figure 7:
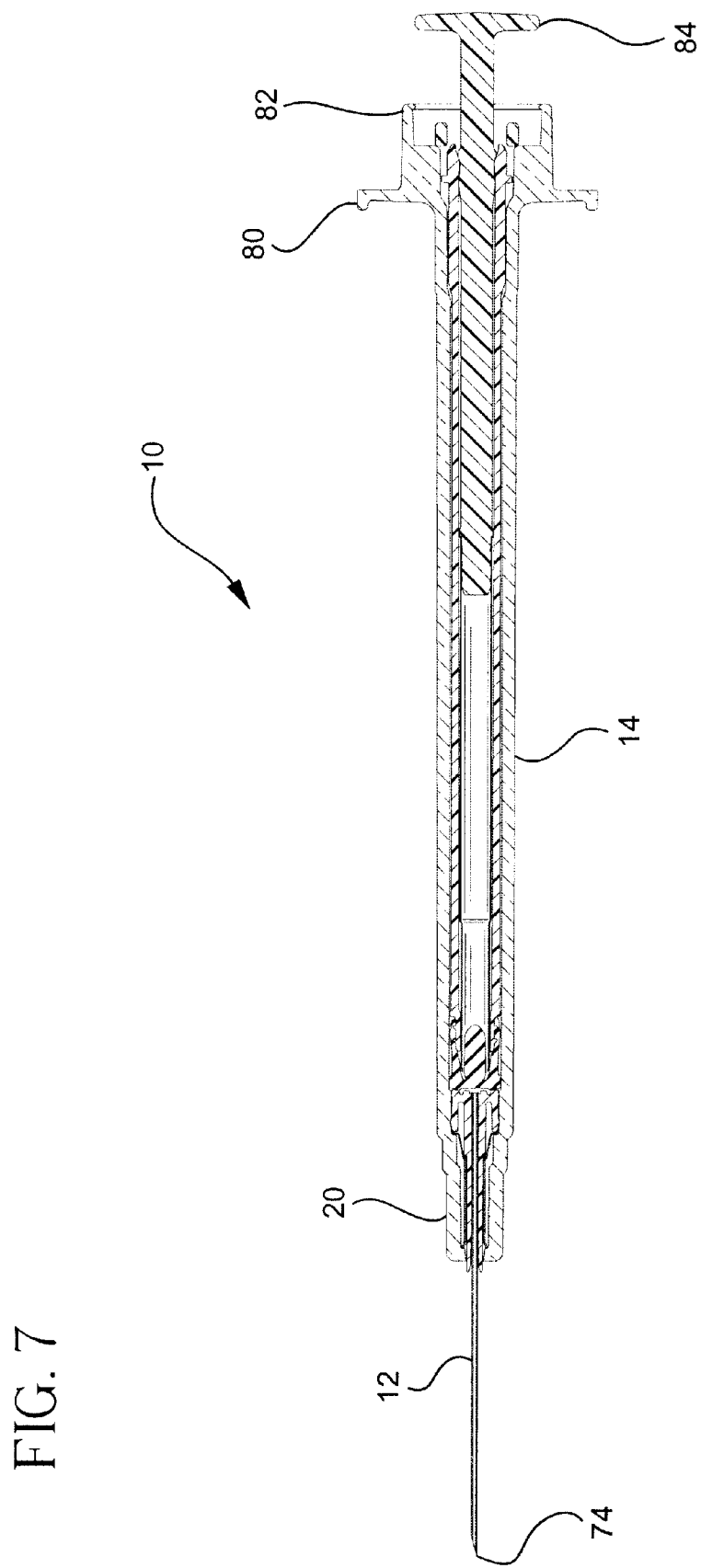
FIG. 7 is a cross-sectional view of the syringe of FIG. 1, analogous to FIG. 4, with the plunger distal in the barrel.
Figure 8:
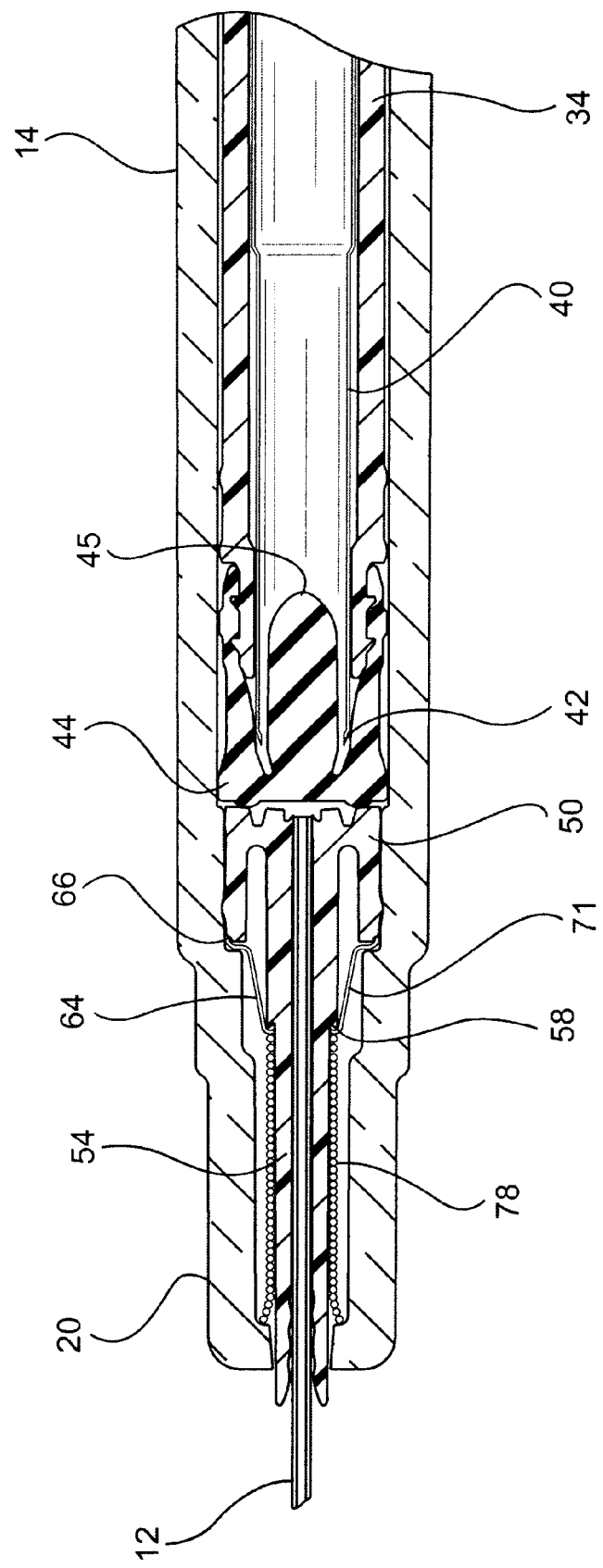
FIG. 8 is an enlarged cross-sectional view of the distal portion of the syringe of FIG. 1, taken from FIG. 7, analogous to FIG. 5.
Figure 9:
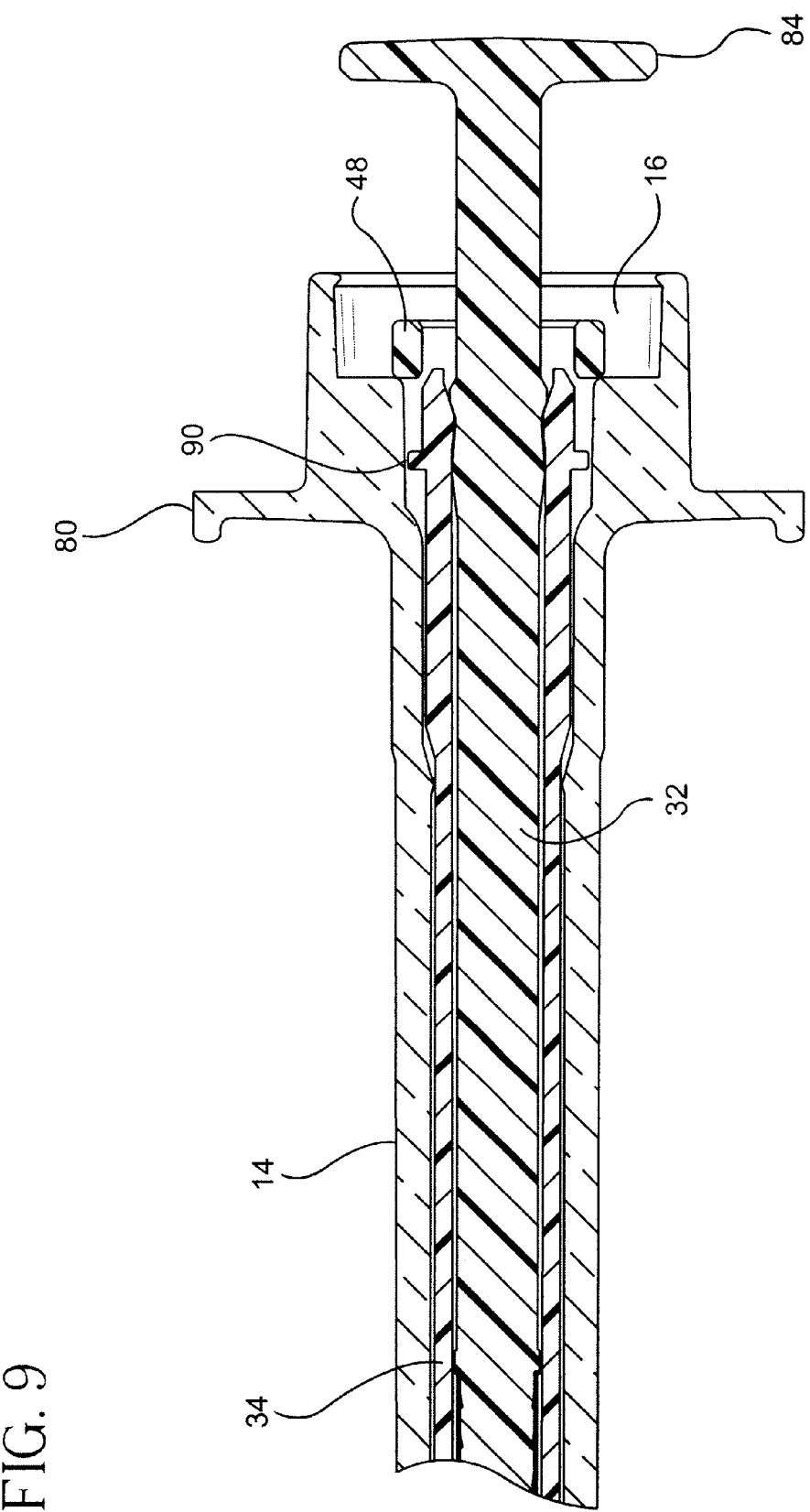
FIG. 9 is a enlarged cross-sectional view of the proximal portion of the syringe of FIG. 1, taken from FIG. 7, analogous to FIG. 6.

Referring now to FIGS. 7–9, views similar to the views of FIGS. 4–6 are shown. In these views, collar 48 is displaced by distal movement of plunger 26 with a force greater than the force necessary to expel fluid from chamber so that collar 48 engages barrel open proximal end 16. When collar 48 is displaced, application of distal force to finger press 84 results in distal movement of inner rod 32 with respect to plunger hollow sleeve 34. This advances hollow cutter 40 to against stopper 44 to cut through the stopper and flange 56.

Figure 10:
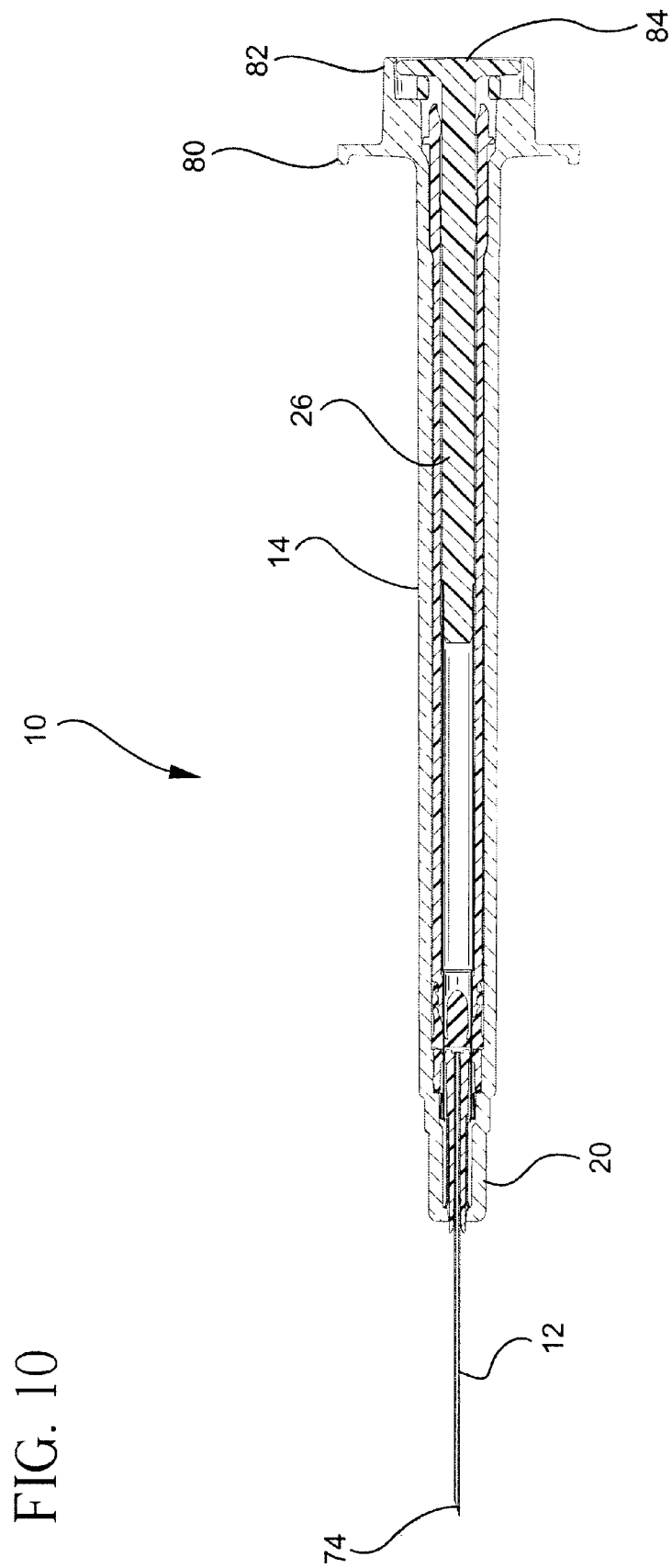
FIG. 10 is a cross-sectional view of the syringe of FIG. 1, analogous to FIG. 4, with the plunger more distal in the barrel than shown in FIG. 7.
Figure 11:
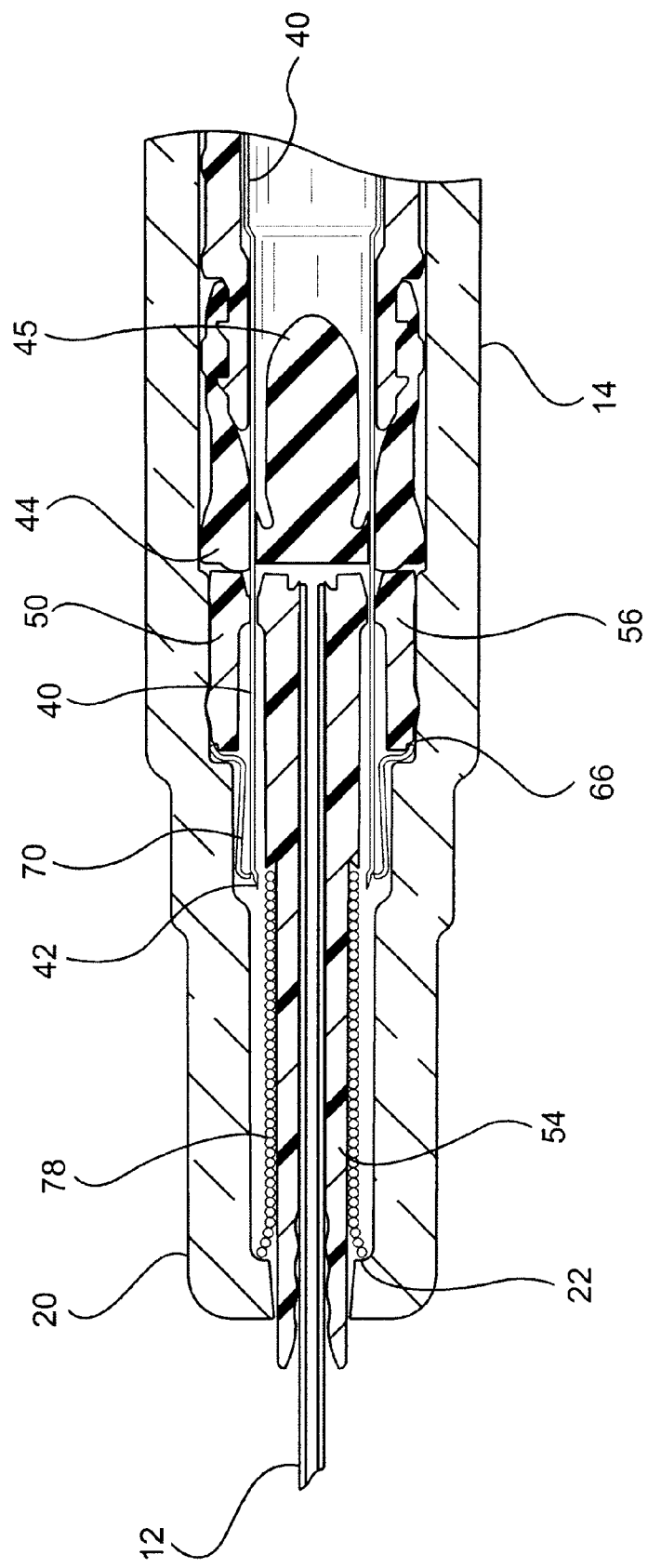
FIG. 11 is an enlarged cross-sectional view of the distal portion of the syringe of FIG. 1, taken from FIG. 10, analogous to FIG. 5.
Figure 12:
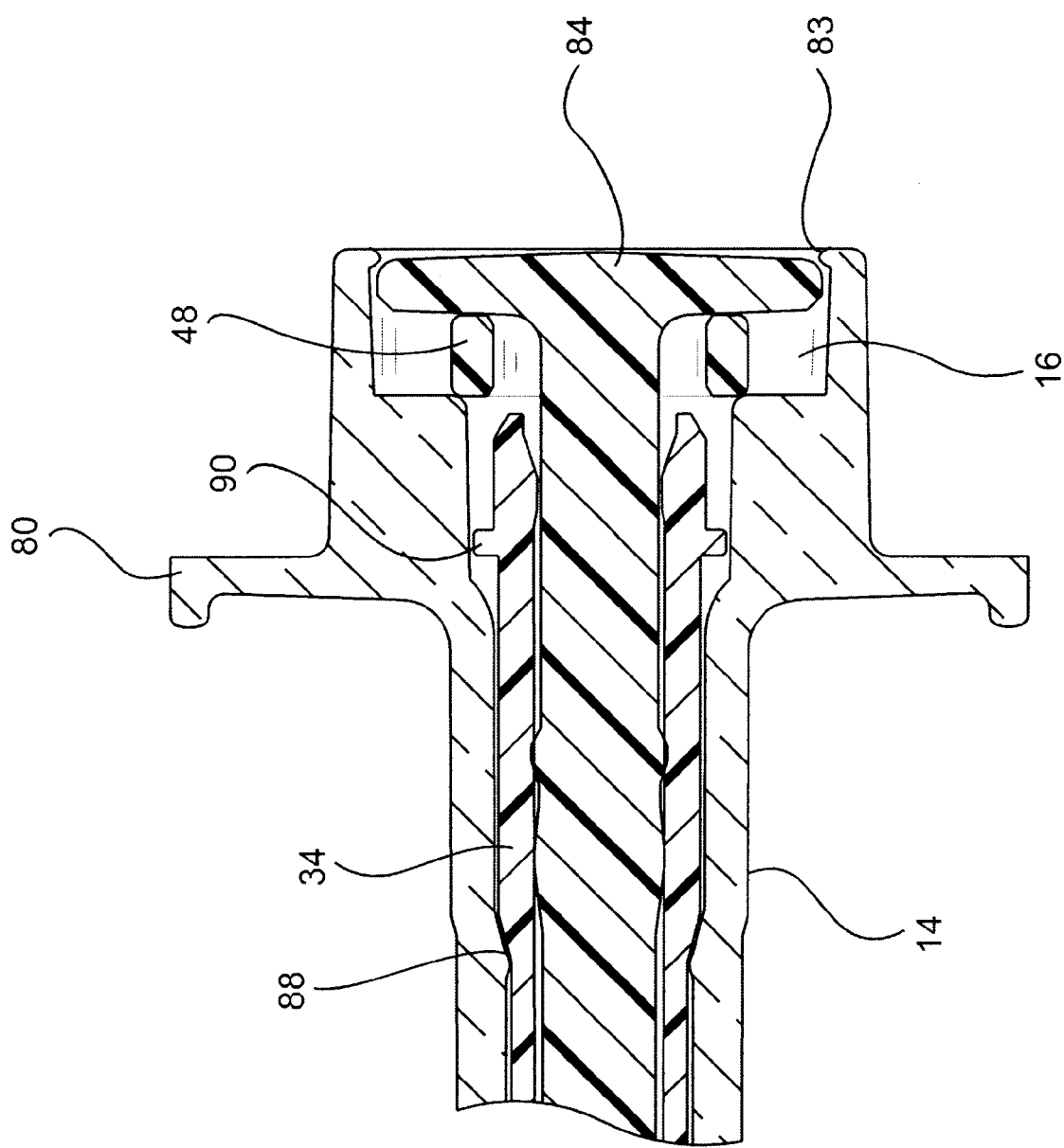
FIG. 12 is an enlarged cross-sectional view of the proximal portion of the syringe of FIG. 1, taken from FIG. 10, analogous to FIG. 6.
Figure 13:
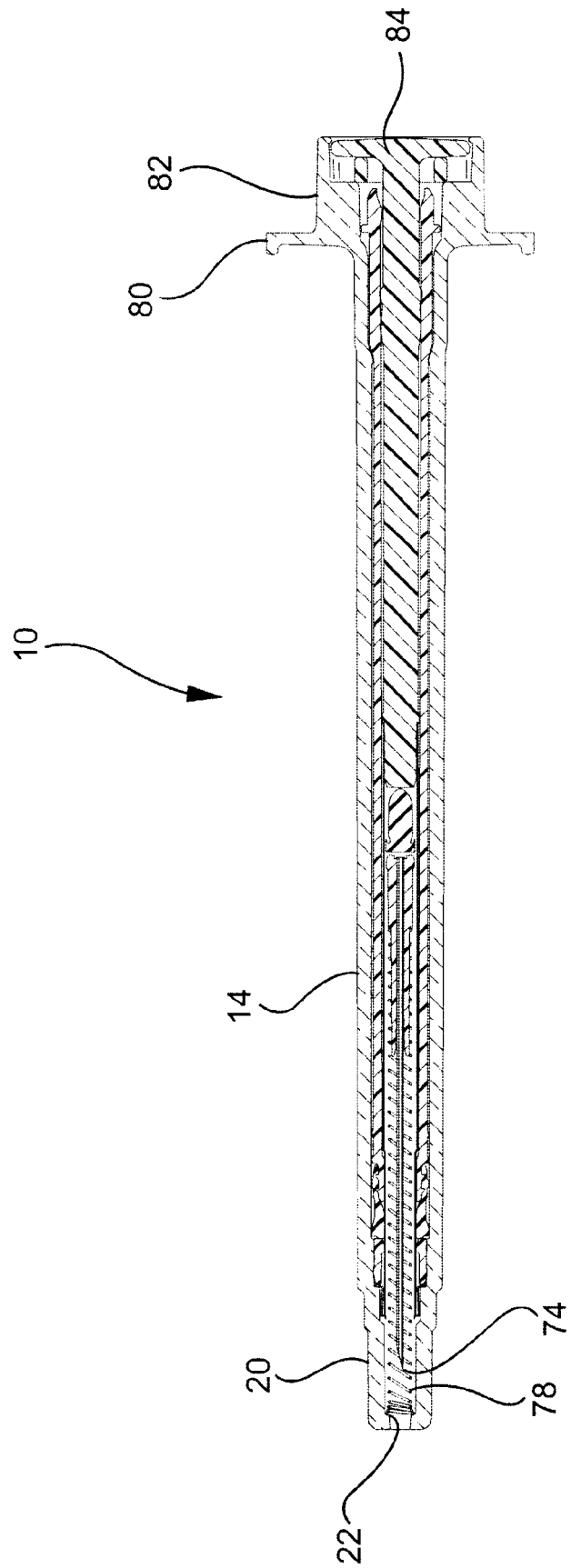
FIG. 13 is a cross-sectional view of the syringe of FIG. 1, analogous to FIG. 4, with the needle withdrawn into the barrel.
Figure 14:
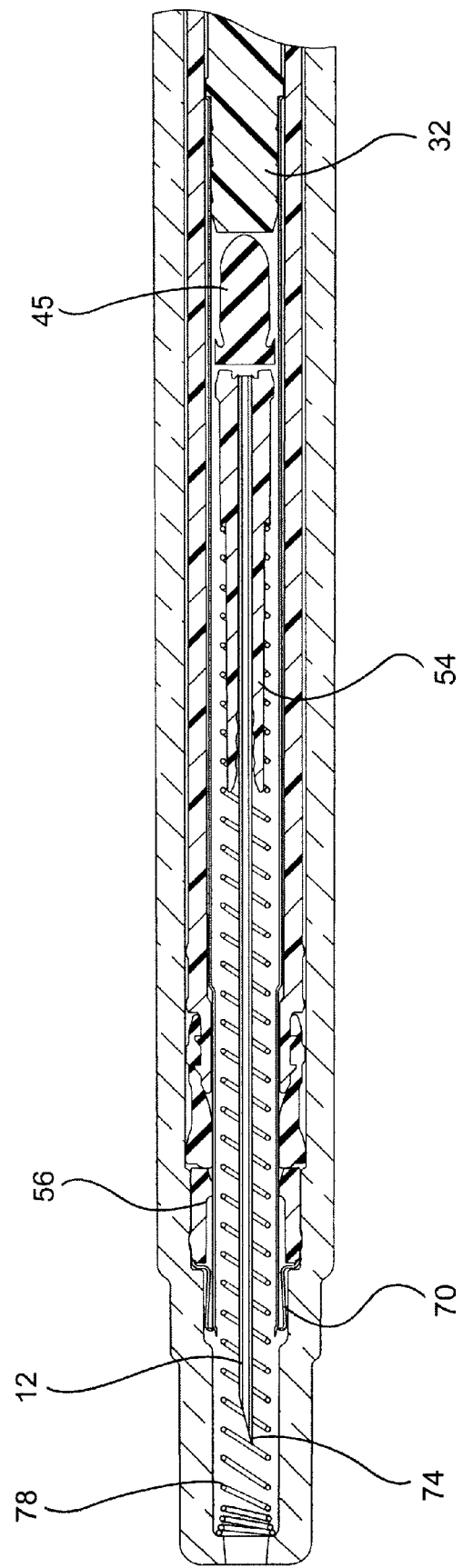
FIG. 14 is an enlarged cross-sectional view of the distal portion of the syringe of FIG. 1, taken from FIG. 13, analogous to FIG. 5.

Referring now to FIGS. 10–12, views similar to the views of FIGS. 4–6 are shown. In these views, collar 48 is fully displaced, finger press 84 is moved distally sufficiently so that finger press 84 is contained within shroud 82. Preferably, shroud 82 has an inside diameter at the proximal end that is less than the outside diameter of finger press 84, thereby providing an interference 83 between the finger press and the shroud. When sufficient force is applied, interference 83 is overcome, and finger press 84 substantially irreversibly enters shroud 82, thereby substantially preventing further proximal movement of the plunger. In FIG. 11, hollow cutter 40 is advanced distally so that cutting surface 42 has cut through stopper 44 and flange 56. After cutting through flange 56, cutting surface 42 is advanced distally to engage clip 64 by passing through clip opening 68 in clip proximal foot 66 to spread clip fingers 71 with distal grips 70 away from engagement 58 on stem 54. Once clip distal grips 70 are spread away from engagement 58, the bias from compressed spring 78 urges the cut portion of the flange and the cut portion of the stopper to move proximally into hollow cutter 40 thereby withdrawing needle 12 to a position where sharpened distal point 74 is substantially within syringe 10 and protected from inadvertent exposure. The withdrawn position for the needle and cut portions is best seen in FIGS. 13 and 14. At this point, syringe 10 substantially cannot be restored to functionality, because finger press 84 is within shroud 82, flange 56 is cut through, stopper 44 is cut through, and spring 78 has been released from a compressed position within receiver 20.

Figure 15:
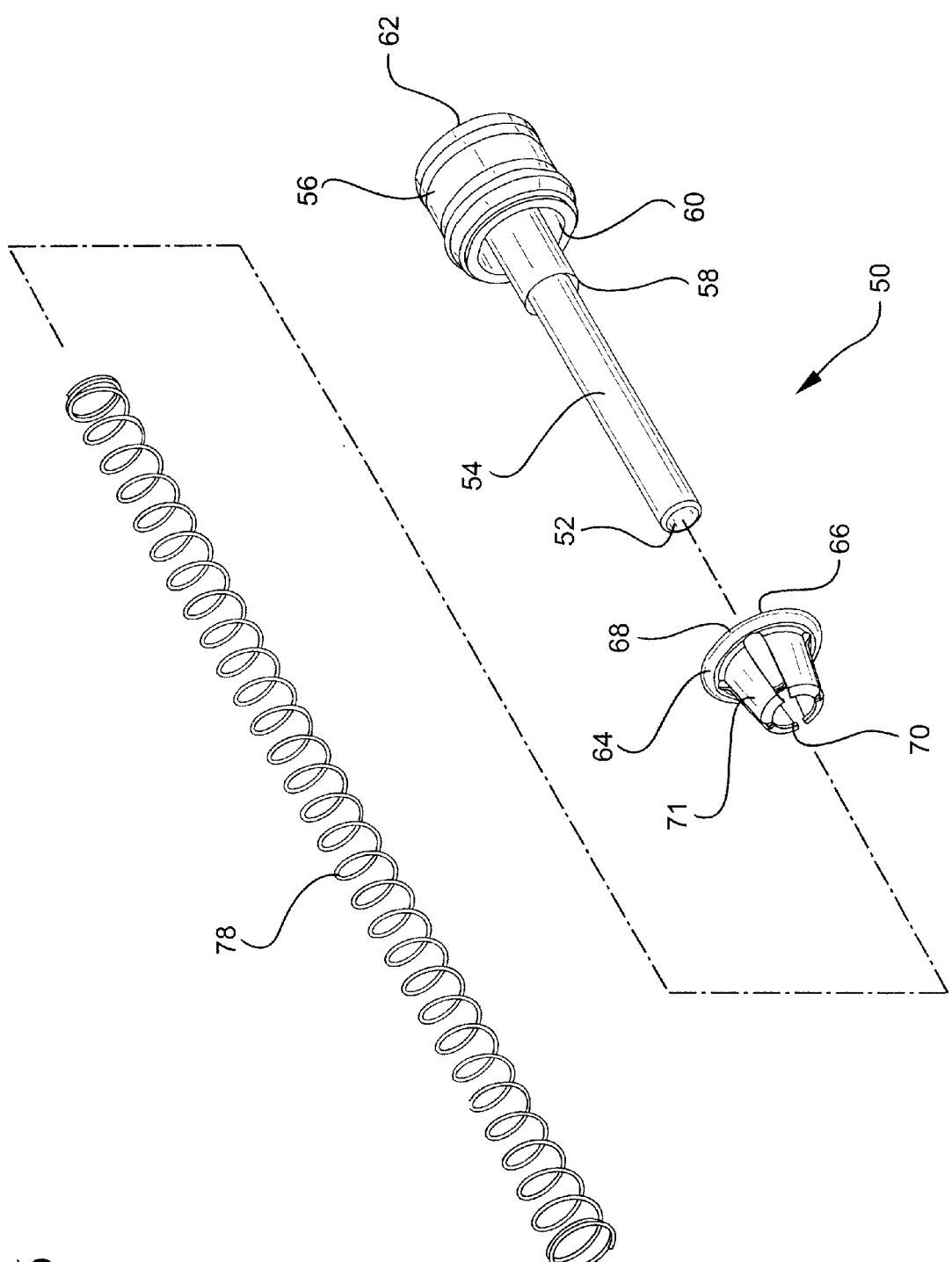
FIG. 15 is an exploded perspective view of the hub portion of the syringe of FIG. 1.

FIG. 15 is an exploded perspective view of the hub assembly showing spring 78, clip 64 and hub 50. Spring 78 is preferably an elongate coil formed from a resilient metallic material such as stainless steel wire. Other materials and other forms of metallic materials may also be suitable and preferred for particular applications. Clip 64 is preferably also formed from a metallic material. Stainless steel is preferred and preferably is formed into the clip by a deep draw stamping process. Clip 64 includes proximal foot 66 with opening 68 therethrough and a plurality, preferably four, distal grips 70 on four fingers 71 to engage stem 54 at engagement 58. After forming, clip 58 is preferably subjected to an electrochemical process for cleaning, polishing, burr removal and to form a sharp surface on grips 70 to engage stem 54. Referring back to FIG. 5, the placement of spring 78, clip 64 and hub 50 within receiver 20 is best seen in syringe 10 in the normal ready for normal use position. Hub 50 is preferably formed from thermoplastic materials including, but not limited to, polypropylene, polystyrene, polyethylene, copolymers and other filled thermoplastic materials.

Figure 16:
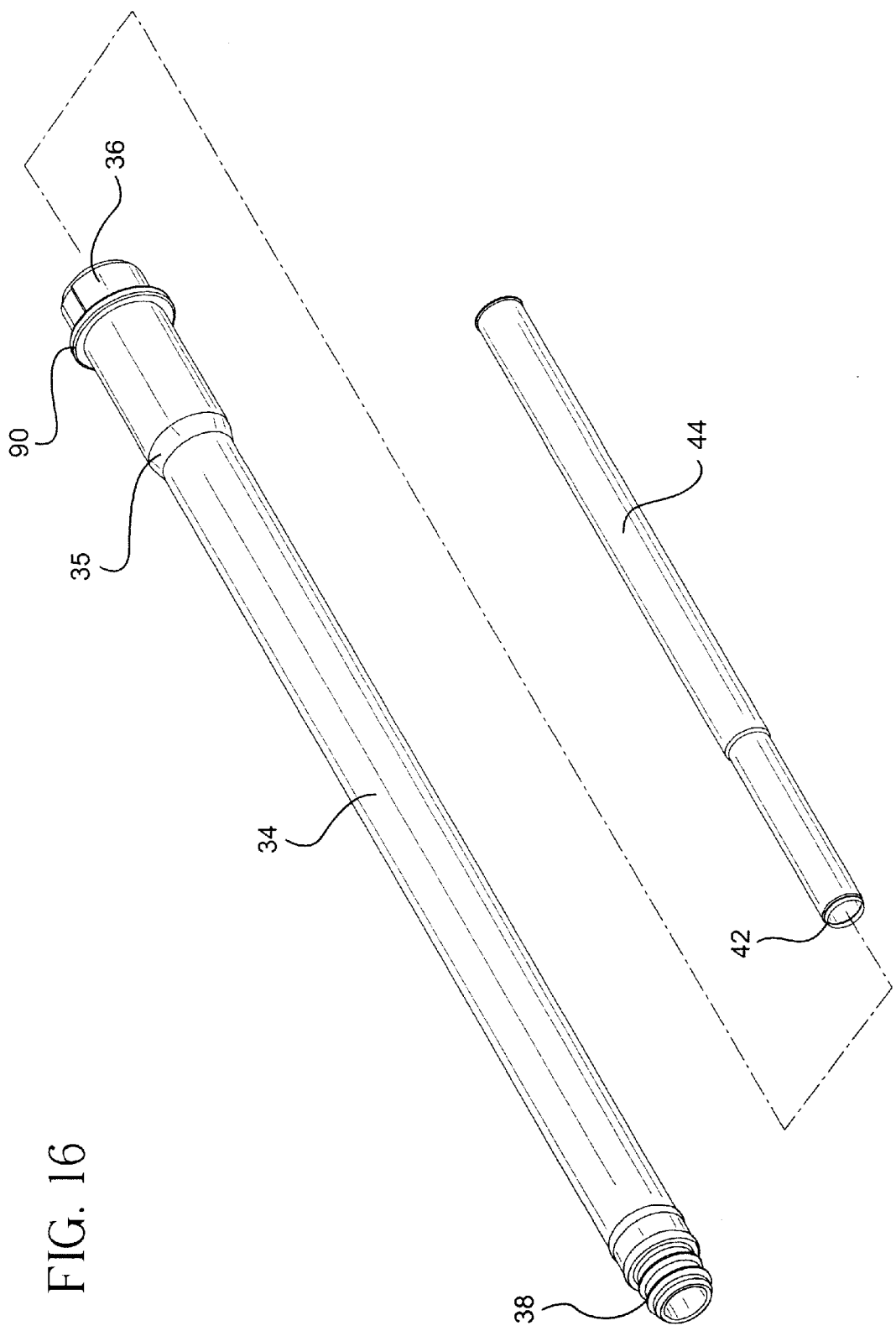
FIG. 16 is an exploded perspective view of the hollow sleeve portion of the plunger of the syringe of FIG. 1.
Figure 17:
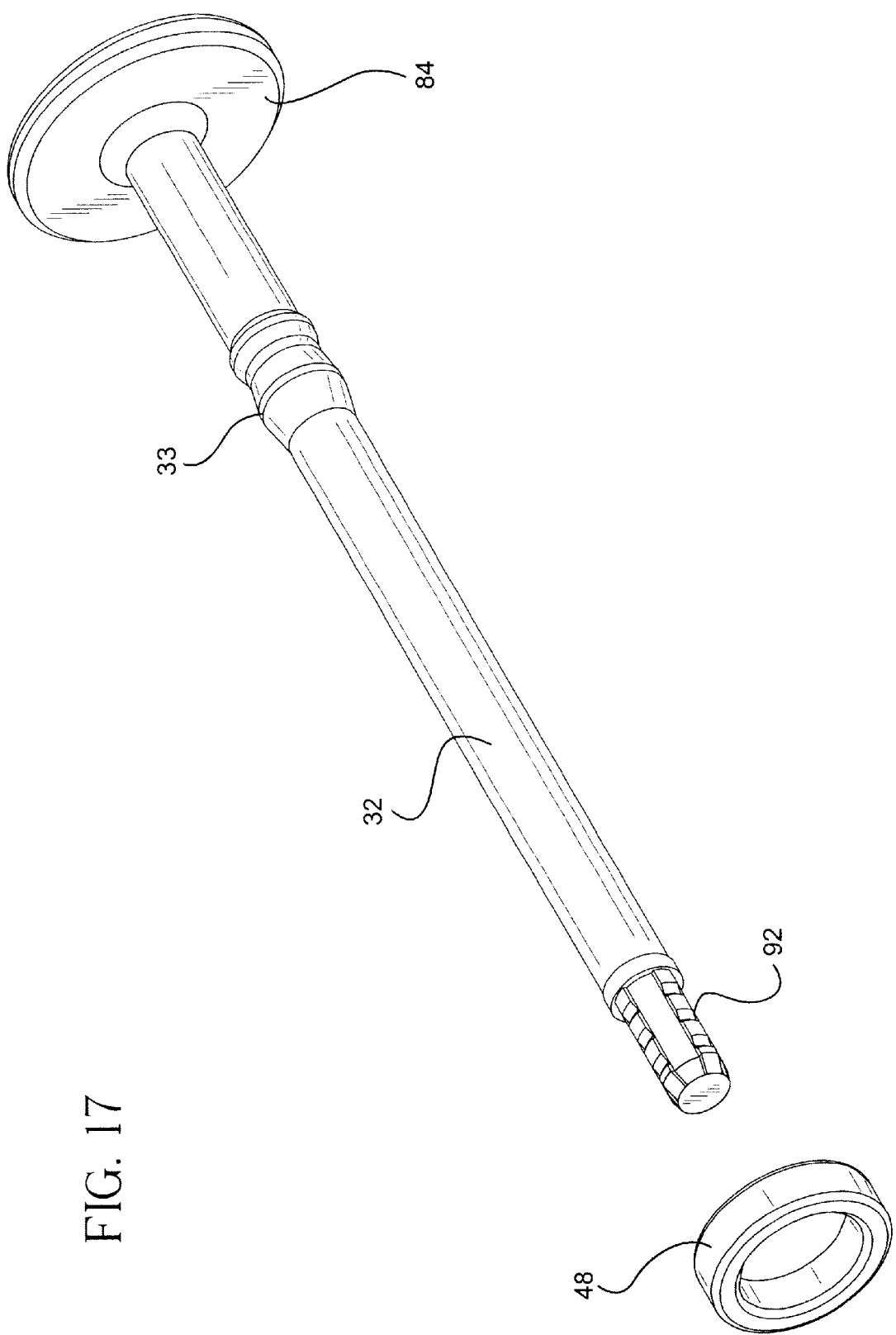
FIG. 17 is an exploded perspective view of the inner rod portion of the syringe of FIG. 1.

FIG. 16 is an exploded perspective view of the plunger hollow sleeve 34 and hollow cutter 40. In this view, proximal end 35 of the hollow sleeve with step 88 to engage proximal end 16 of the barrel is seen. Hollow sleeve 34 also includes a shoulder 90 to limit distal travel of displaceable collar 48 when the collar 48 is disposed to prevent movement of plunger inner rod 32 with respect to hollow sleeve 34 when syringe 10 is in normal use for drawing and expelling fluids. Referring now to FIG. 17, plunger inner rod 32 is shown along with collar 48. Plunger inner rod includes a distal mount 92 for mounting hollow cutter 40 so that when plunger 26 is assembled with inner rod 32 within hollow sleeve 34, cutting surface 42 is proximal to the surface of stopper 44, best seen in FIG. 5 and collar 48 is positioned at shoulder 90 to substantially prevent movement between the inner rod and hollow sleeve so that stopper 44 is moved proximally and distally within barrel 14 to draw and expel fluid from chamber 46.

Hollow sleeve 34 and plunger inner rod 32 preferably are formed from thermoplastic materials such as polystyrene, polypropylene, polycarbonate, polyacetal and the like. Copolymers and filled thermoplastic materials are also suitable. The use of the inner rod and the outer sleeve tied together by collar 48 allows plunger 26 to be sufficiently stiff for normal usage of drawing and expelling fluids, because inner rod 32 may be solid and integrally formed with finger press 84. Collar 84, also preferably formed from thermoplastic materials including, but not limited to, polypropylene, polycarbonate, polyethylene, polystyrene, copolymers and the like, is displaced by contact with proximal end 16 of the barrel. When collar 84 is displaced, inner rod 32 advances distally with respect to hollow sleeve 34 and hollow cutter 40 with cutting surface 42 is advanced into plunger 44 and flange 56. Hollow cutter 40 is preferably formed from a metallic material thus able to be "thin-walled" to provide a maximum space to receive cut plunger 44 and cut flange 56. Deep-drawn stainless steel is a preferred material and method for forming hollow cutter 40. After forming, hollow cutter 40 preferably may be subjected to a sharpening process to provide a sharp surface for cutting surface 42. Suitable sharpening processes include, but are not limited to, honing, grinding, buffing, electrochemical treatments, combinations of these processes and the like. Electrochemical treatments are preferred, because, in addition to providing a sharp cutting surface, they may be controlled to provide a cleaning and polishing effect on the rest of the surface of the hollow cutter.

A method for assembling syringe 10 with selectively retractable needle 12 includes providing an elongate barrel 14 with open proximal end 16 and open distal end 18 defining receiver 20 with distal inward shoulder 22. The method further includes providing elongate hub 50 with a passageway 52 therethrough and including distal elongate stem portion 54 with engagement 58 and proximal flanged portion 56 having a conjugate 57 to the retention 25 on the inside surface of hollow bore 24. A mandrel is then inserted into the barrel from distal end 18, elongate spring 78 is placed onto the mandrel, clip 64 is placed onto the mandrel proximal to spring 78. Distal stem 54 is then inserted into proximal end 16 of the barrel so that stem 54 contacts the mandrel. The assembly method then includes moving the mandrel and hub 50 distally so that the mandrel is removed from barrel 14, clip 64 contacts engagement 58, and spring 78 is thereby compressed between clip 64 and shoulder 22 on receiver 20. Bump 25 on the inside surface of the barrel engages depression 57 on flange 56 thereby retaining hub 50 in the barrel.

The particular benefits of plunger 26 of the invention with the hollow sleeve 34, hollow cutter 40 and inner rod 32 are apparent when FIGS. 4, 5 and 6 are considered. In one preferred embodiment of syringe 10 of the invention, where syringe 10 is a one milliliter capacity syringe graduated in tenths of a milliliter, the overall length of the syringe is less than about five inches with the exterior diameter less than about one quarter inch. When barrel 10 is formed from the preferred thermoplastic material, polypropylene, the interior diameter of barrel 10 is about 0.183 inches. When the information related to earlier work in the area of retractable syringes, summarized in the instant background section, is reviewed, it should be apparent that most of these previously disclosed designs could not be readily fit within an interior diameter barrel of 0.183 inches and manufactured on a scale of several millions a week. Plunger 26 is assembled as a separate unit and is inserted into proximal end 16 of the barrel in a similar fashion to conventional assembly of plungers and barrels into syringes.

Figure 3:
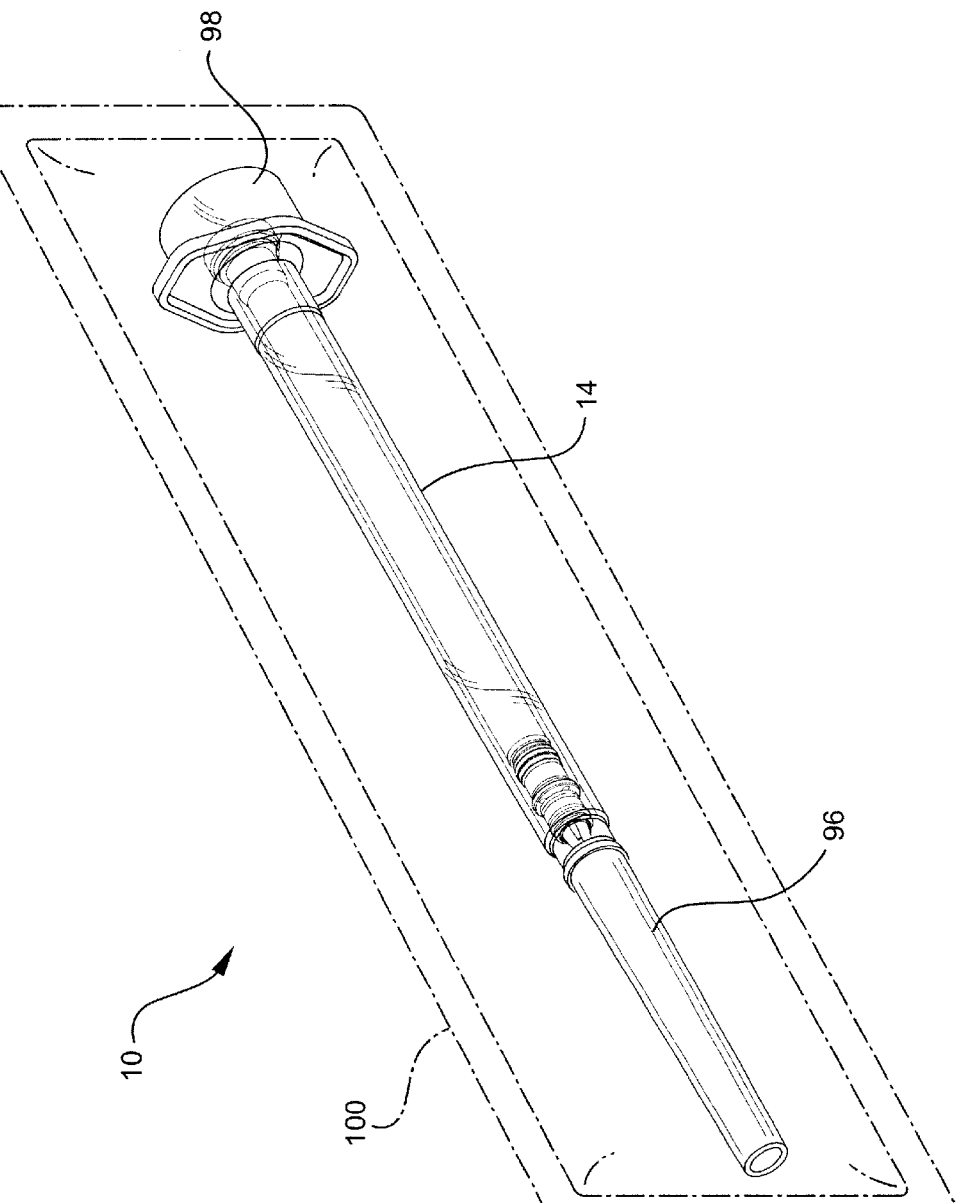
FIG. 3 is a perspective view of the syringe of FIG. 1 with a cap and shield sealed in a package.

Referring now to FIG. 3, syringe 10 of the invention may be removably fit with a needle shield 96 sized to fit receiver 20 and a removable cap 98 sized to fit shroud 82. Cap 98 and shield 96 may be frangibly attached by heat staking, labeling or the like, to the shroud and receiver so that the interior of syringe 10 is substantially protected from microorganisms and exposed to conditions that substantially render microorganisms non-viable and sold as "self-contained". The frangible attachments of the cap and shield to the shroud and receiver providing a user with "tamper-evidence" that the cap and shield have not been removed. A further refinement is to seal syringe 10 with shield 96 and with or without cap 98 in a package 100 formed from materials substantially resistant to the passage of microorganisms. Sealed package 100 may be exposed to conditions that render any microorganisms therein substantially non-viable. Syringe 10 then may be considered "sterile" as long as package 100 is unopened. Suitable materials for forming package 100 include, but are not limited to paper, nonwovens, polymeric film, metallic foils and combinations of these materials. Suitable conditions for rendering microorganisms non-viable include ionizing radiation, such as gamma and electron beam, chemical agents such as ethylene oxide, gaseous hydrogen peroxide and the like. When selecting materials for forming syringe 10 and package 100, consideration should be given to the method of sterilization to ensure that the materials and the sterilization conditions are compatible.

Syringe 10 of the invention provides users, particularly users of small diameter low dead space syringes, widely used outside of normal medical situations for self injection of insulin, with a syringe that is usable in a normal fashion for the medicament delivery. Once the delivery is completed by the user, the user selectively applies additional distal force to finger press 84, greater than the force required to expel fluid from chamber 46, displaces collar 48 from the position where it prevents movement of inner rod 32 with respect to plunger hollow sleeve 34, and initiates a substantially irreversible process that causes the withdrawal of needle 12 to within the syringe, thereby substantially protecting anyone coming into contact with syringe 10 from inadvertent exposure to pointed distal end 74 of the needle and substantially eliminating any subsequent reuse of syringe 10.

What is claimed is:

1. A hypodermic syringe with a selectively retractable needle comprises:

an elongate barrel having an open proximal end and a distal end defining a receiver having a distal inward shoulder, said barrel having a hollow bore therethrough extending from said proximal end to said distal end;

an elongate plunger having a proximal end and a distal end, said plunger including an inner rod extending a distance distally from said proximal end, a hollow sleeve having a proximal end and a distal end, sized to fit slidably, extend beyond and disposed over said inner rod, a hollow cutter extending distally from said inner rod to a distal cutting surface within said hollow sleeve, and a stopper disposed over said distal end of said hollow sleeve to cover said cutting surface, said stopper being sized to fit slidably within said hollow bore of said barrel to define a chamber to draw and expel fluid, said plunger further including a displaceable collar that substantially prevents a movement of said inner rod with respect to said hollow sleeve, said collar being displaced by application of a distal force, greater than a force required to expel fluid from said chamber in said barrel, to said plunger, said collar being displaced by engagement with said proximal end of said barrel, and, when said collar is displaced, allows a movement with respect to said hollow sleeve of said inner rod having said cutter attached thereto, and causes said cutting surface to cut through said stopper;

an elongate hub having a stem with a proximal flange and an engagement, said stem disposed within and sized for slidable movement within said receiver at said distal end of said barrel with said flange having a distal surface and a proximal surface, said proximal surface of said flange defining a distal end of said chamber in said barrel, said hub having a passageway therethrough;

a clip having a proximal foot with an opening therethrough and a distal grip, said clip being disposed on said stem of said hub with said proximal foot at said distal surface of said flange and said grip at said engagement on said stem;

an elongate needle having a fluid path therethrough, said needle having a pointed distal end and a proximal end mounted in said passageway of said hub so that said pointed end of said needle extends distally outwardly and said fluid path of said needle is in fluid communication with said chamber of said barrel;

an elongate spring disposed about said stem of said hub compressed between said receiver and said distal grip of said clip to provide a bias, so that when sufficient distal force, greater than the force needed to expel fluid from said chamber, is applied to said plunger to cause said cutting surface to cut through said stopper, said cutting surface then engages said flange and cuts through said flange thereby to engage said clip and to cause said clip to release said engagement on said stem and to allow said bias of said spring to urge a sufficient movement of said hub to a position within said syringe where inadvertent contact with said pointed distal end of the needle is substantially prevented.

2. The hypodermic syringe of claim 1 wherein said hollow cutter has an inside diameter at said proximal end and said distal end, wherein inside diameter at said distal end is smaller than said inside diameter between said proximal end and said distal end, said flange proximal surface includes a groove for engaging said cutting surface so that as said cutting surface cuts through said stopper, said stopper is stretched, thereby cutting a section from said stopper smaller than said inside diameter of said cutting surface.

3. The hypodermic syringe of claim 1 wherein said displaceable collar is disposed on said plunger at a detent formed by a cooperating depression and an enlargement on either one of an outside surface of said inner rod and an inside surface of said hollow sleeve, said collar serving to keep said depression and said enlargement in cooperative engagement when said collar is in position, thereby substantially to prevent a movement of said inner rod with respect to said hollow sleeve, and to allow a disengagement of said enlargement and said depression when said collar is displaced, thereby to allow said movement of said inner rod with respect to said hollow sleeve.

4. The hypodermic syringe of claim 1 wherein said distal grip of said clip comprises a plurality of fingers extending from said proximal foot to contact said engagement on said stem, said fingers being spread outwardly apart by movement of said cutter through said opening in said foot to release said engagement on said stem, thereby allowing said spring to contact said engagement on said stem so that said bias of said spring urges proximal movement of said hub into said syringe.

5. The hypodermic syringe of claim 1 wherein said proximal end of said barrel further includes a finger flange for assisting a user's grip of said syringe during use.

6. The hypodermic syringe of claim 5 wherein said finger flange further includes a shroud having an inside diameter disposed and shaped to received a removable cap for covering said plunger and wherein said receiver at said distal end of said barrel is shaped to receive a removable shield for protecting said sharp distal point of said needle.

7. The hypodermic syringe of claim 6 wherein said cap and said shield are frangibly attached to said shroud and said shroud and said receiver respectively, so that neither said cap nor said shield are removable from said shroud and said receiver respectively without disruption of said attachments, thereby providing a positive evidence to user that once said cap and said shield are positioned on said shroud and said receiver, they have not been removed prior to the intended use, thereby providing a "tamper-evidence" and substantially prevent passage of microorganisms into said fluid path of said syringe, said syringe being exposed to conditions that render any microorganisms therein substantially non-viable.

8. The hypodermic syringe of claim 7 wherein said plunger further comprises a proximal finger press having an outside diameter and wherein when said distal force greater than the force required to expel fluid from the chamber is applied to said plunger, said finger press substantially irreversibly enters said shroud, thereby substantially preventing said plunger from being inadvertently removed.

9. The hypodermic syringe of claim 8 wherein said shroud further includes a proximal inwardly projecting shoulder defining an inside diameter less than said outside diameter of said finger press, thereby providing an interference fit between said shroud and said finger press so that when said user applies the distal force greater than the force required to expel fluid said chamber, said interference is overcome and said finger press substantially irreversibly enters said shroud thereby being retained by said shoulder.

10. The hypodermic syringe of claim 1 wherein said spring is formed from a metallic material shaped into an elongate coil.

11. The hypodermic syringe of claim 1 wherein said hollow cutter and said clip are formed from a metallic material.

12. The hypodermic syringe of claim 11 wherein said metallic material for forming said hollow cutter and said clip is stainless steel.

13. The hypodermic syringe of claim 12 wherein at least one of said hollow cutter and said clip are each subjected to a secondary process selected from the group consisting of electrochemical processing, deburring, grinding, honing and combinations thereof after forming.

14. The hypodermic syringe of claim 1 wherein said stopper is formed from a resilient material selected from the group consisting of natural rubber, thermoplastic elastomer, synthetic rubber and combinations thereof.

15. The hypodermic syringe of claim 1 wherein said hollow bore of said barrel has an inside surface having at least one depression therein and said flange on said hub has a conjugate projection thereon so that when said hub is disposed in said receiver at said distal end of said barrel with said spring compressed between said clip and said shoulder on said receiver, said depression engages said projection to retain said hub in said barrel.

16. A method for assembling a hypodermic syringe with a selectively retractable needle comprises:
providing an elongate barrel having an open proximal end and an open distal end defining a receiver with a distal inward shoulder, said barrel having a hollow bore therethrough extending from said proximal end to said distal end, said hollow bore having an inside surface having retention means;
providing an elongate hub having a passageway there through, said hub including a distal elongate stem portion with an engagement and a proximal flanged portion having a conjugate to said retention means on said inside surface of said hollow bore;
inserting a mandrel into said barrel from said distal end;
placing an elongate spring onto said mandrel;
placing a clip onto said mandrel proximal to said spring;
inserting said distal stem portion of said hub into said barrel so that said stem contacts said mandrel;
moving said mandrel and said hub distally so that said mandrel is removed from said barrel, said clip contacts said engagement, said spring thereby being compressed between said clip and said shoulder on said receiver and said retention means on said inside surface of said barrel engages said conjugate on said flange, thereby retaining said hub in said barrel.

17. The method of claim 16 further comprising placing an elongate needle having a sharpened distal point, a proximal end and a fluid path therethrough into said passageway in said hub so that said sharpened distal point extends distally outwardly and said fluid path is in communication with said hollow bore of said barrel.

18. The method of claim 17 further comprising assembling an elongate plunger having a proximal end and a distal end, said plunger including an inner rod extending a distance distally from said proximal end, a hollow sleeve having a proximal end and a distal end, sized to slidably fit, extend beyond and disposed over said inner rod, a hollow cutter extending distally from said inner rod to a distal cutting surface within said hollow sleeve, and a stopper disposed over said distal end of said hollow sleeve to cover said cutting surface, said stopper being sized to fit slidably within said hollow bore of said barrel to define a chamber to draw and expel fluid, said plunger further including a displaceable collar that substantially prevents a movement of said inner rod with respect to said hollow sleeve, said collar being displaced by application of a distal force, greater than a force required to expel fluid from said chamber in said barrel, to said plunger, said collar being displaced by engagement with said proximal end of said barrel, and wherein when said collar is displaced, allows a movement with respect to said hollow sleeve of said inner rod having said cutter attached thereto, and causes said cutting surface to cut through said stopper; and
inserting said distal end of said plunger into said proximal end of said barrel.

19. A method for causing a withdrawal of a needle into a syringe barrel comprises:
expressing the contents of a syringe barrel by application of a distal force to a syringe plunger disposed in said barrel comprising a proximal end and a distal end, said plunger having an inner rod extending a distance distally from said proximal end, a hollow sleeve having a proximal end and a distal end, sized to slidably fit, extend beyond and disposed over said inner rod, a hollow cutter extending distally from said inner rod to a distal cutting surface within said hollow sleeve, and a stopper disposed over said distal end of said hollow sleeve to cover said cutting surface, said stopper being sized to fit slidably within said hollow bore of said barrel to define a chamber to draw and expel fluid, said plunger further including a displaceable collar that substantially prevents a movement of said inner rod with respect to said hollow sleeve, said collar being displaced is by application of a distal force, greater than a force required to expel fluid from said chamber in said barrel, to said plunger, said collar being displaced by engagement with said proximal end of said barrel, and, when said collar is displaced, allows a movement with respect to said hollow sleeve of said inner rod having said cutter attached thereto, and causes said cutting surface to cut through said stopper;
applying additional distal force to said plunger thereby displacing said collar thereby allowing said cutter on said sleeve to cut through said stopper.

* * * * *